(12) United States Patent  
Razavi et al.

(10) Patent No.: US 7,439,205 B2  
(45) Date of Patent: Oct. 21, 2008

(54) TRIDENTATE METAL CATALYST FOR OLEFIN POLYMERIZATION

(75) Inventors: Abbas Razavi, Mons (BE); Vladimir Marin, Houston, TX (US); Margarito Lopez, Pasadena, TX (US)

(73) Assignee: Fina Technology, Inc., Houston, TX (US)

( * ) Notice: Subject to any disclaimer, the term of this patent is extended or adjusted under 35 U.S.C. 154(b) by 60 days.

(21) Appl. No.: 11/285,479

(22) Filed: Nov. 21, 2005

(65) Prior Publication Data

US 2007/0117943 A1    May 24, 2007

(51) Int. Cl.  
*C08F 4/72*    (2006.01)

(52) U.S. Cl. ................. 502/155; 502/167; 526/161; 526/171; 556/51

(58) Field of Classification Search ........... 502/155, 502/167; 526/161, 171; 556/51  
See application file for complete search history.

(56) References Cited

U.S. PATENT DOCUMENTS

| 6,103,657 A | 8/2000 | Murray |
| 2003/0191012 A1 | 10/2003 | Murray |

FOREIGN PATENT DOCUMENTS

| WO | PCT/GB99/03152 |   | 9/1999 |
| WO | WO 00/20427 | * | 4/2000 |

* cited by examiner

*Primary Examiner*—Robert D. Harlan  
(74) *Attorney, Agent, or Firm*—Tenley R. Krueger

(57) ABSTRACT

In accordance with the present invention, there is provided a transition metal olefin polymerization catalyst component characterized by the formula:

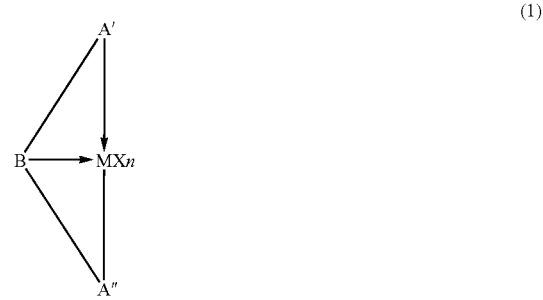

(1)

where, M is a Group IV or a Group IV transition metal, B is a bridge group containing at least two carbon atoms, A' and A" are organogroups, each containing a heteroatom selected from the group consisting of oxygen, sulfur, nitrogen and phosphorus, X is selected from the group consisting of chlorine, bromine, iodine, a $C_1$-$C_{20}$ alkyl group, a $C_6$-$C_{30}$ aromatic group and mixtures thereof, and n is 1, 2 or 3. The invention also encompasses a method for the polymerization of an ethylenically unsaturated monomer which comprises contacting a transition metal catalyst component as characterized by formula (1) above and an activating co-catalyst component in a polymerization reaction zone with an ethylenically unsaturated monomer under polymerization conditions to produce a polymer product.

17 Claims, No Drawings

TRIDENTATE METAL CATALYST FOR OLEFIN POLYMERIZATION

FIELD OF THE INVENTION

This invention relates to olefin polymerization catalysts incorporating tridentate pyridinyl transition metal catalyst components, and more particularly tridentate bis- and mono-imino pyridinyl ligand structures and their use in polymerization.

BACKGROUND OF THE INVENTION

Polymers of ethylenically unsaturated monomers such as polyethylene or polypropylene homopolymers and ethylene-propylene copolymers may be produced under various polymerization conditions and employing various polymerization catalysts. Such polymerization catalysts include Ziegler-Natta catalysts and non-Ziegler-Natta catalysts, such as metallocenes and other transition metal catalysts which are typically employed in conjunction with one or more co-catalysts. The polymerization catalysts may be supported or unsupported.

Homopolymers or copolymers of alpha olefins may be produced under various conditions in polymerization reactors which may be batch type reactors or continuous reactors. Continuous polymerization reactors typically take the form of loop-type reactors in which the monomer stream is continuously introduced and a polymer product is continuously withdrawn. For example, the production of polymers such as polyethylene, polypropylene or ethylene-propylene copolymers involve the introduction of the monomer stream into the continuous loop-type reactor along with an appropriate catalyst system to produce the desired homopolymer or copolymer. The resulting polymer is withdrawn from the loop-type reactor in the form of a "fluff" which is then processed to produce the polymer as a raw material in particulate form as pellets or granules. It is often the practice in the production of ethylene homopolymers and ethylene $C_{3+}$ alpha olefin copolymers to employ substantial amounts of molecular weight regulators such as hydrogen to arrive at polymers or copolymers of the desired molecular weight. Typically in the polymerization of ethylene, hydrogen may be employed as a regulator with the hydrogen being introduced into the monomer feed stream in amounts of about 10 mole % and higher of the ethylene feed stream.

SUMMARY OF THE INVENTION

In accordance with the present invention, there is provided a transition metal olefin polymerization catalyst component characterized by the formula:

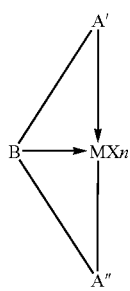

(1)

In formula (1), M is a Group IV or a Group IV transition metal and the structure A', A" and B provides a coordination ligand structure containing heteroatoms selected from the group consisting of oxygen, sulfur, nitrogen and phosphorus, which are bonded to the metal M. In the ligand structure, B is a bridge group containing at least two carbon atoms, which provides an electron donative relationship with respect to the transition metal M and forms a structural bridge between A' and A", imparting stereorigidity to the ligand structure. A' and A" are organogroups, each containing a heteroatom selected from the group consisting of oxygen, sulfur, nitrogen and phosphorus. A' is sigma-bonded with the bridge group B and multi-electron bonded to the metal M. A" is sigma-bonded to the bridge group and to the transition metal M. In formula (1), X is selected from the group consisting of chlorine, bromine, iodine, a $C_1$-$C_{20}$ alkyl group, a $C_6$-$C_{30}$ aromatic group and mixtures thereof, and n is 1, 2 or 3. In a specific embodiment of the invention, B is a substituted or unsubstituted pyridinyl group coordinated with the transition metal M through the nitrogen atom of the pyridinyl group. The pyridinyl group, B, is bridged to A' and A" through carbon atoms of the pyridinyl group which are proximal to the nitrogen atom of the pyridinyl group.

In a more specific aspect of the invention, the catalyst component is characterized by the formula:

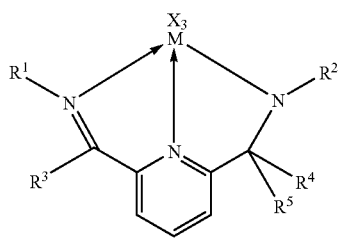

(2)

In formula (2), $R^1$ and $R^2$ are the same or different and are each a $C_1$-$C_{20}$ alkyl group, a $C_4$-$C_{20}$ cycloalkyl group, or a substituted or unsubstituted aryl group having from 6-30 carbon atoms; $R^3$ and $R^4$ are the same or different and are each a hydrogen, $C_1$-$C_{20}$ alkyl group, a $C_4$-$C_{20}$ cycloalkyl group, or a substituted or unsubstituted aryl group having from 6-30 carbon atoms; and $R^5$ is alkyl group, a $C_4$-$C_{20}$ cycloalkyl group, a benzyl group or a substituted or unsubstituted aryl group having from 6-30 carbon atoms. X and M are as defined above. In a preferred embodiment, the catalyst component is characterized by the formula:

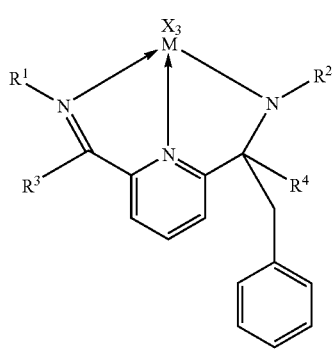

(3)

wherein $R^1$, $R^2$, $R^3$, $R^4$, X and M are as defined above.

In another embodiment of the invention, $R^3$ and $R^4$ of formula (3) are methyl groups and $R^1$ and $R^2$ are each a substituted phenyl group, a substituted naphthyl group or a substituted anthracene group to provide a catalyst component having the structural formula (4):

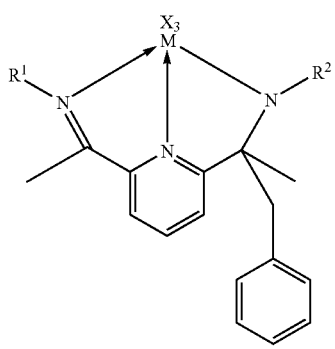

(4)

In yet a further embodiment of the invention, the catalyst component is similar to those depicted by formulas (2), (3) and (4) above, except that the C=N double bond is displaced one carbon atom outward from the C=N double bond of formulas (2), (4) and (7). In this embodiment, the catalyst components are characterized by the structural formula (5):

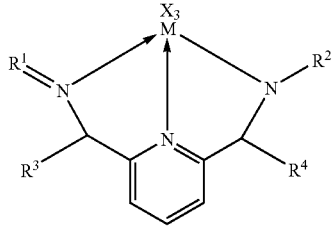

(5)

and more specifically, by the structural formula (6):

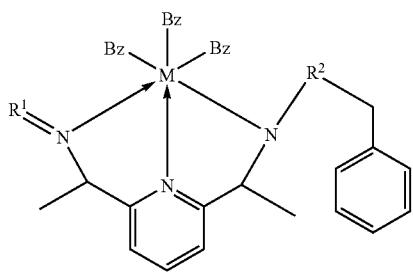

(6)

In formula (5), $R^1$ and $R^2$ are the same or different and are each a $C_1$-$C_{20}$ alkyl group, a $C_4$-$C_{20}$ cycloalkyl group, or a substituted or unsubstituted aryl group having from 6-30 carbon atoms; $R^3$ and $R^4$ are the same or different and are each a hydrogen, $C_1$-$C_{20}$ alkyl group, a $C_4$-$C_{20}$ cycloalkyl group, or a substituted or unsubstituted aryl group having from 6-30 carbon atoms; and X is an alkyl group, an aryl group, or a halogen. In formula (6), $R^1$ and $R^2$ are the same and are a $C_4$-$C_{20}$ cycloalkyl group, or a substituted or unsubstituted aryl group. In a more specific embodiment of this aspect of the invention, in the catalyst component characterized by the formula (6), $R^1$ and $R^2$ are the same and are:

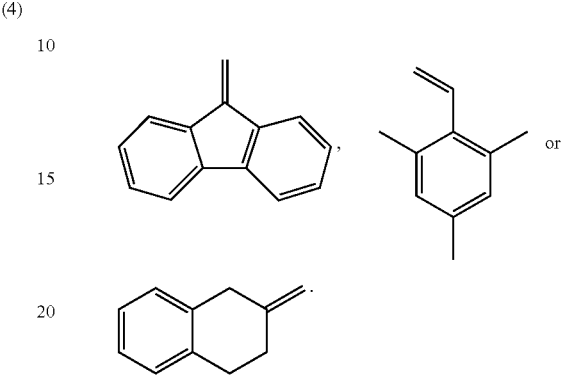

In another embodiment of the invention, the catalyst component characterized by formula (1) incorporates a mono-imine ligand structure and is characterized by formula (7):

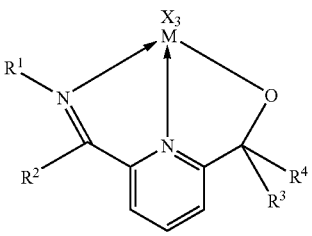

(7)

In formula (7), $R^1$, $R^2$, $R^3$, $R^4$, X and M are as defined above. In a more specific embodiment of this aspect of the invention, $R^4$ is a methyl group and $R^3$ is a benzyl group.

In yet a further embodiment of the invention, there is provided a method for the polymerization of an ethylenically unsaturated monomer which comprises providing a transition metal catalyst component as characterized by formula (1) above and providing an activating co-catalyst component. The catalyst component and the co-catalyst component are contacted in a polymerization reaction zone with an ethylenically unsaturated monomer under polymerization conditions to produce a polymer product by the polymerization of the monomer. In a preferred application of this embodiment of the invention, the transition metal catalyst component is characterized by formula (3) above in which X is a benzyl group and the alpha olefin is ethylene. In one embodiment of the invention, the polymer product is an ethylene homopolymer. In another embodiment of the invention, the catalyst component and co-catalyst component are contacted with ethylene and a $C_{3+}$ alpha olefin having from 3-20 carbon atoms to produce a copolymer of ethylene and the $C_{3+}$ alpha olefin. In another embodiment of the invention, the polymer product is a propylene homopolymer.

DETAILED DESCRIPTION OF THE INVENTION

The present invention involves bridged catalyst components characterized by the formula:

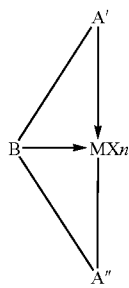

(1)

in which A', A" and B provides a coordination ligand structure containing heteroatoms selected from the group consisting of oxygen, sulfur, nitrogen and phosphorous, which are bonded to the transition metal M. The catalyst components as characterized by formula (1) can be described as non-metallocene catalyst compounds in that they do not require r bonding of the transition metal through the use of cyclopentadienyl rings. As described in greater detail below, the ligand structure incorporating the heteroatom groups A' and A" preferably involve nitrogen in one organogroup and either oxygen or nitrogen in the other organogroup. These structures may be shown schematically by the following schematic formulas:

In the foregoing structural formulas (1') and (1"), A' and A" denote the organogroup in which the nitrogen atom or the oxygen atom or present. In the following discussion, the catalyst components are of the type characterized by formula (1') or (1"). However, it is to be recognized that one or both nitrogen atoms in the hetero-organogroup may be replaced by phosphorous atoms. Similarly, an oxygen atom in the hetero-organogroup, OA", may be replaced by a sulfur group to produce the corresponding bridged thio-ligand structure.

As described below, the preferred ligand structures depicted by formula (1') or (1") are pyridinyl amine-imine ligands as characterized by the formula:

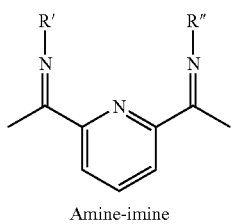

Amine-imine or oxo-imine ligands as characterized by the formula:

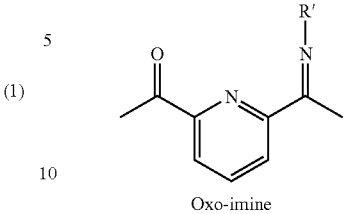

Oxo-imine

Specific embodiments of these imino ligand structures are exemplified by the catalyst components identified below as catalyst components C1-C11. While nitrogen atoms in these catalyst components can be replaced by phosphorous atoms and oxygen atoms by sulfur atoms, the preferred catalyst components will incorporate bis-imino or mono-imino ligand structures as described above.

The catalyst components of the present invention may be employed in the polymerization of an ethylenically unsaturated monomer, such as ethylene or propylene, or in the copolymerization of such monomers with a second polymer. Thus, the catalyst component may be employed in the polymerization of ethylene or propylene to produce polyethylene homopolymer, polypropylene homopolymer or copolymers of ethylene or propylene. Suitable monomer systems include ethylene and a $C_{3+}$ alpha olefin having from 3 to 20 carbon atoms. Thus, copolymers of ethylene and 1-hexene may be produced, for example.

In employing the catalyst components of the present invention in polymerization procedures, they are used in conjunction with an activating co-catalyst. Suitable activating co-catalysts may take the form of co-catalysts such are commonly employed in metallocene-catalyzed polymerization reactions. Thus, the activating co-catalyst may take the form of an alumoxane co-catalyst. Alumoxane co-catalysts are also referred to as aluminoxane or polyhydrocarbyl aluminum oxides. Such compounds include oligomeric or polymeric compounds having repeating units of the formula:

where R is an alkyl group generally having 1 to 5 carbon atoms. Alumoxanes are well known in the art and are generally prepared by reacting an organo-aluminum compound with water, although other synthetic routes are known to those skilled in the art. Alumoxanes may be either linear polymers or they may be cyclic, as disclosed for example in U.S. Pat. No. 4,404,344. Thus, alumoxane is an oligomeric or polymeric aluminum oxy compound containing chains of alternating aluminum and oxygen atoms whereby the aluminum carries a substituent, preferably an alkyl group. The structure of linear and cyclic alumoxanes is generally believed to be represented by the general formula —(Al(R)—O-)-m for a cyclic alumoxane, and $R_2Al$—O—(Al(R)—O)m-$AlR_2$ for a linear compound wherein R independently each occurrence is a $C_1$-$C_{10}$ hydrocarbyl, preferably alkyl or halide and m is an integer ranging from 1 to about 50, preferably at least about 4. Alumoxanes also exist in the configuration of cage or cluster compounds. Alumoxanes are typically the reaction products of water and an aluminum alkyl, which in addition to an alkyl group may contain halide or alkoxide groups. Reacting several different aluminum alkyl compounds, such as, for example, trimethylaluminum and tri-isobutylaluminum, with water yields so-called modified or mixed alumoxanes. Preferred alumoxanes are methylalumoxane and methylalumoxane modified with minor amounts of other higher alkyl groups such as isobutyl. Alumoxanes generally contain minor to substantial amounts of the starting aluminum alkyl compounds. The preferred co-catalyst, prepared either from trimethylaluminum or tri-isobutylaluminum, is sometimes referred to as poly(methylaluminum oxide) and poly(isobutylaluminum oxide), respectively.

The alkyl alumoxane co-catalyst and transition metal catalyst component are employed in any suitable amounts to provide an olefin polymerization catalyst. Suitable aluminum transition metal mole ratios are within the range of 10:1 to 20,000:1 and preferably within the range of 100:1 to 2,000:1. Normally, the transition metal catalyst component and the alumoxane, or other activating co-catalyst as described below, are mixed prior to introduction in the polymerization reactor in a mode of operation such as described in U.S. Pat. No. 4,767,735 to Ewen et al. The polymerization process may be carried out in either a batch-type, continuous or semi-continuous procedure, but preferably polymerization of the ethylene will be carried out in a loop-type reactor of the type disclosed in the aforementioned U.S. Pat. No. 4,767,735. Typical loop-type reactors include single loop reactors or so-called double loop reactors in which the polymerization procedure is carried in two sequentially connected loop reactors. As described in the Ewen et al. patent, when the catalyst components are formulated together, they may be supplied to a linear tubular pre-polymerization reactor where they are contacted for a relatively short time with the pre-polymerization monomer (or monomers) prior to being introduced into the main loop type reactors. Suitable contact times for mixtures of the various catalyst components prior to introduction into the main reactor may be within the range of a few seconds to 2 days. For a further description of suitable continuous polymerization processes which may be employed in carrying out the present invention, reference is made to the aforementioned U.S. Pat. No. 4,767,735, the entire disclosure of which is incorporated herein by reference.

Other suitable activating co-catalysts which can be used in carrying out the invention include those catalysts which function to form a catalyst cation with an anion comprising one or more boron atoms. By way of example, the activating co-catalyst may take the form of triphenylcarbenium tetrakis (pentafluorophenyl) boronate as disclosed in U.S. Pat. No. 5,155,080 to Elder et al. As described there, the activating co-catalyst produces an anion which functions as a stabilizing anion in a transition metal catalyst system. Suitable noncoordinating anions include $[W(PhF_5)]^-$, $[Mo(PhF_5)]^-$ (wherein PhF5 is pentafluorophenyl), $[ClO_4]^-$, $[S_2O_6]^-$, $[PF_6]^-$, $[SbR_6]^-$, $[AlR_4]^-$ (wherein each R is independently Cl, a $C_1$-$C_5$ alkyl group preferably a methyl group, an aryl group, e.g. a phenyl or substituted phenyl group, or a fluorinated aryl group). Following the procedure described in the Elder et al. patent, triphenylcarbenium tetrakis(pentafluorophenyl)boronate may be reacted with pyridinyl-linked bis-imino ligand of the present invention in a solvent, such as toluene, to produce a coordinating cationic-anionic complex. For a further description of such activating co-catalyst, reference is made to the aforementioned U.S. Pat. No. 5,155,080, the entire disclosure of which is incorporated herein by reference.

In addition to the use of an activating co-catalyst, the polymerization reaction may be carried out in the presence of a scavenging agent or polymerization co-catalyst which is added to the polymerization reactor along with the catalyst component and activating co-catalyst. These scavengers can be generally characterized as organometallic compounds of metals of Groups IA, IIA, and IIIB of the Periodic Table of Elements. As a practical matter, organoaluminum compounds are normally used as co-catalysts in polymerization reactions.

Specific examples include triethylaluminum, tri-isobutylaluminum, diethylaluminum chloride, diethylaluminum hydride and the like. Scavenging co-catalysts normally employed in the invention include methylalumoxane (MAO), triethylaluminum (TEAL) and tri-isobutylaluminum (TIBAL).

The catalyst components may be employed in homogeneous polymerization systems or in heterogeneous systems in which the catalyst components may be supported on suitable supports, such as silica. In addition, hydrogen may be introduced into the polymerization reaction zone as a molecular weight regulator.

In experimental work respecting the present invention, Group IV metal catalysts in which the Group IV metal was titanium, zirconium or hafnium were prepared by reacting tetrabenzyl Group IV metal complexes $(M(CH_2Ph)_4)$ of tridentate bis-(N,N,N) and mono-(O,N,N) imino-pyridine ligands to arrive at the metal component. The tridentate ligand structures were synthesized by the condensation reaction of 2,6-diacetyl pyridine with two equivalents of the corresponding amines for the bis-imine ligands as characterized by the formula:

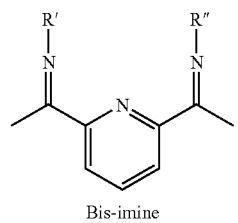

Bis-imine or with one equivalent of the corresponding amines for the mono-imine ligand structure characterized by the following formula:

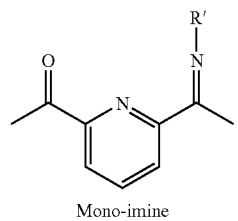

Mono-imine

The reaction routes are illustrated schematically by the following schematic to produce ligands identified as ligands L1, L2, L3 and L4 for the bis-imines and ligands L5 and L6 for the mono-imines:

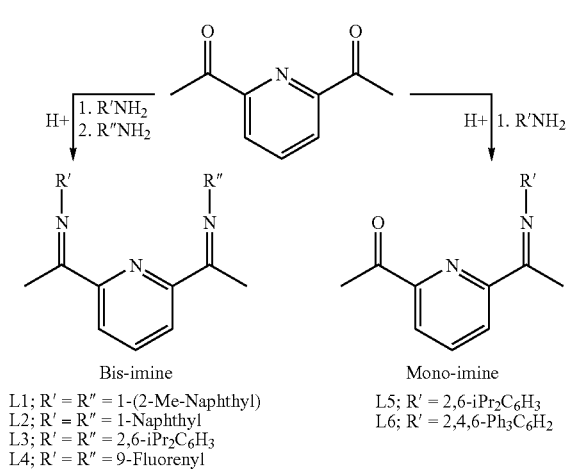

Bis-imine

L1; R' = R'' = 1-(2-Me-Naphthyl)
L2; R' = R'' = 1-Naphthyl
L3; R' = R'' = 2,6-iPr$_2$C$_6$H$_3$
L4; R' = R'' = 9-Fluorenyl Mono-imine L5; R' = 2,6-iPr$_2$C$_6$H$_3$
L6; R' = 2,4,6-Ph$_3$C$_6$H$_2$ Bis-imine ligands identified below as L7, L8 and L9 in which the C═N double bond is displaced one carbon atom outward from double bonds shown in ligands C1-C4 were prepared by the condensation reaction of 2,6-(1,1'-diethylamino)-pyridine with two equivalents of the corresponding cyclic ketone as indicated by the following reaction route:

The tetrabenzyl Group IV metal complexes were synthesized by the reaction of four equivalents of the Grignard reagent, benzylmagnesium chloride, with the Group IV tetrachloride metals in diethyl ether at a temperature of about −20° C. in an atmosphere shielded from light by the following reaction route:

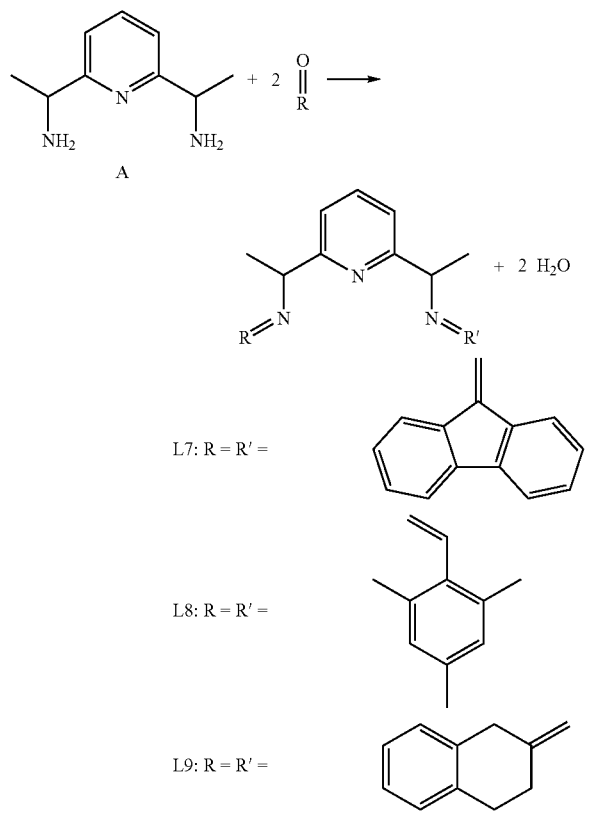

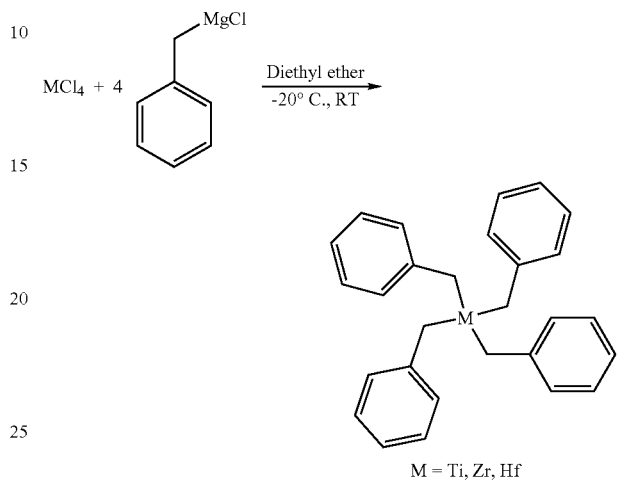

The synthesis of the Group IV metal complexes was achieved by the reaction of one equivalent of the tetrabenzyl metal complex, $M(CH_2Ph)_4$, in which M was titanium, zirconium or hafnium, in benzene with one equivalent of the bis-imine or mono-imine ligands at ambient temperature conditions. The reaction mixture was stirred for at least 16 hours and aliquots of the product were employed for nuclear magnetic resonance characterizations to identify the catalyst components. The foregoing reaction schemes and the corresponding metal complexes identified herein as catalyst components C1-C11 are illustrated schematically as follows:

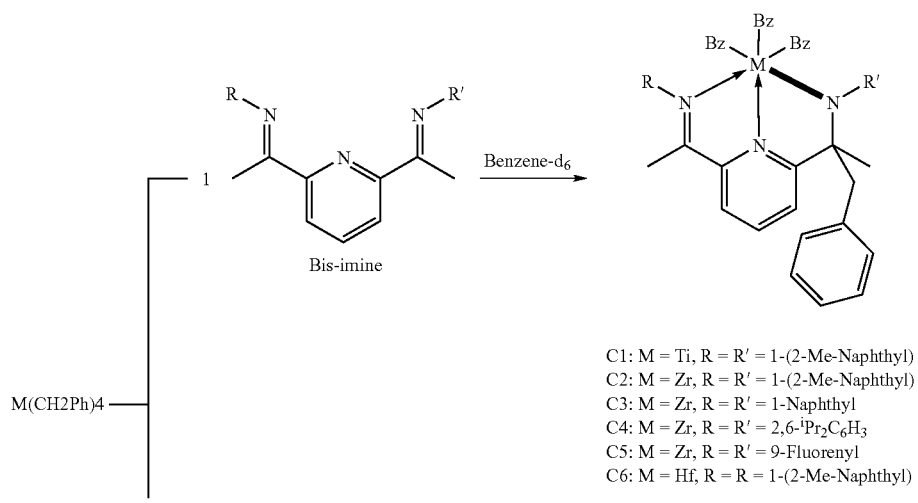

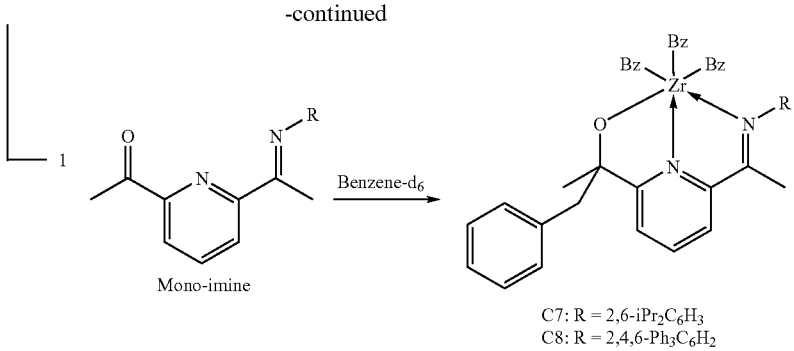
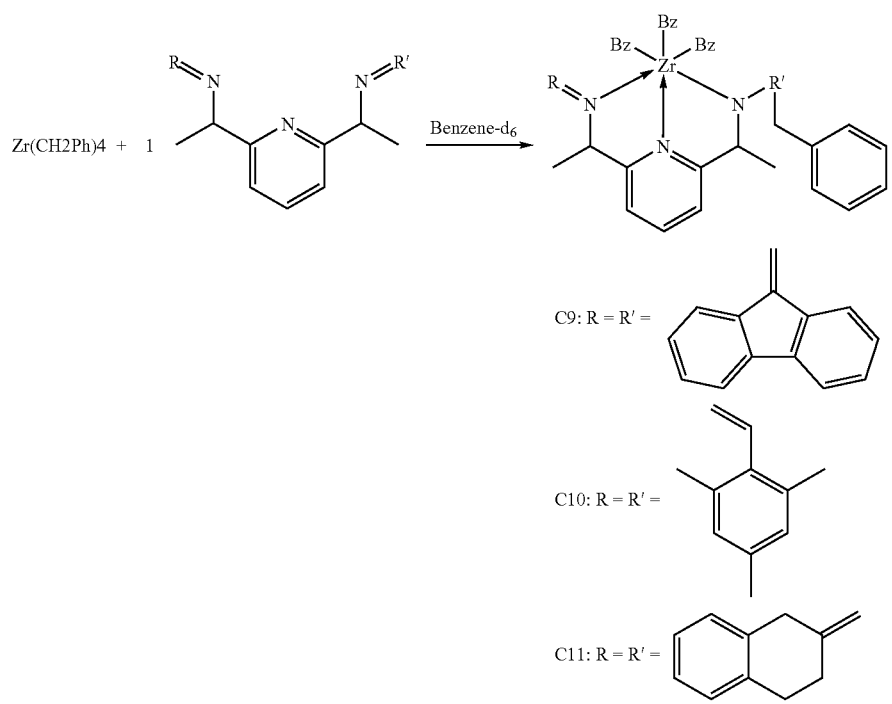
Structural formulas for the catalyst components C1-C11 are indicated below. In the following structural formulas, a methyl group is indicated by /, an isopropyl group by ⋏, and a tertiary butyl group by ⋎.
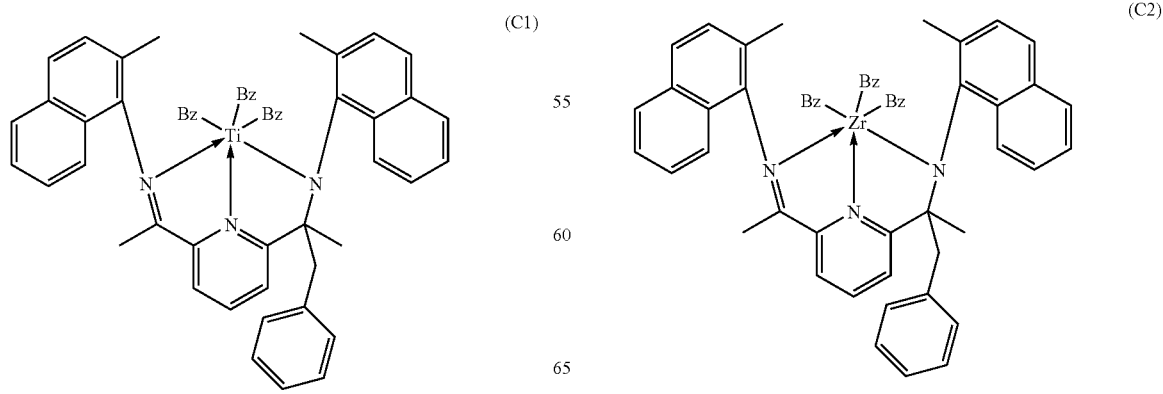

-continued
(C3)
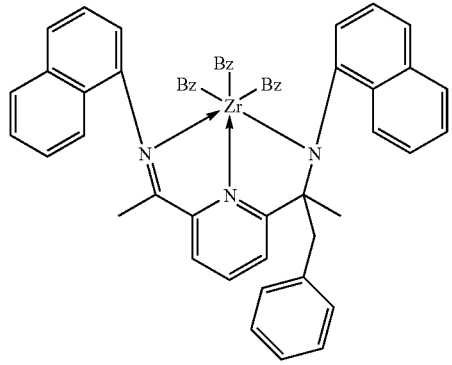
(C4)
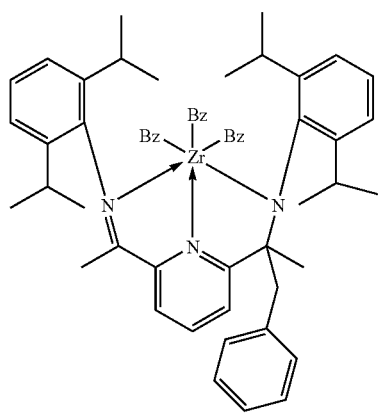
(C5)
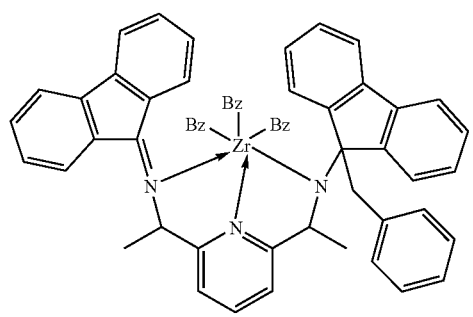
(C6)
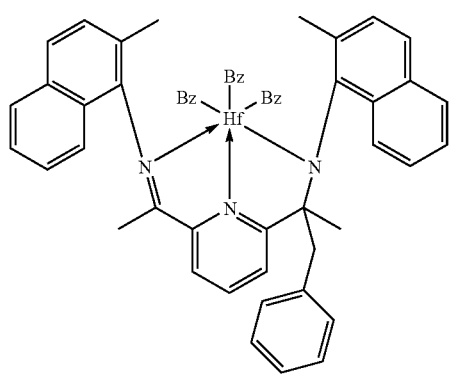
-continued
(C7)
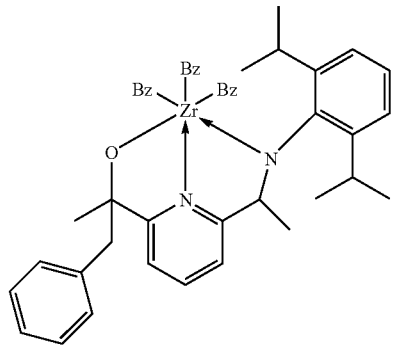
(C8)
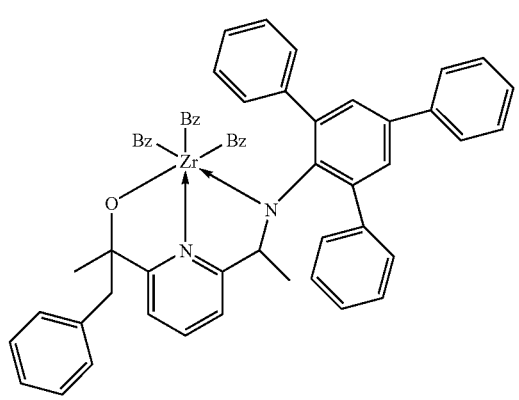
(C9)
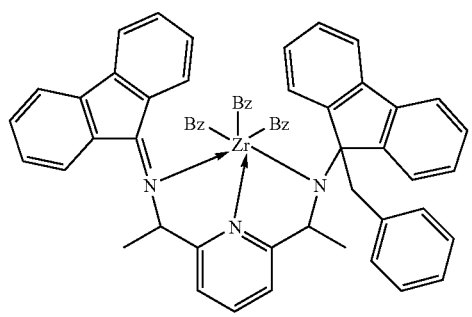
(C10)
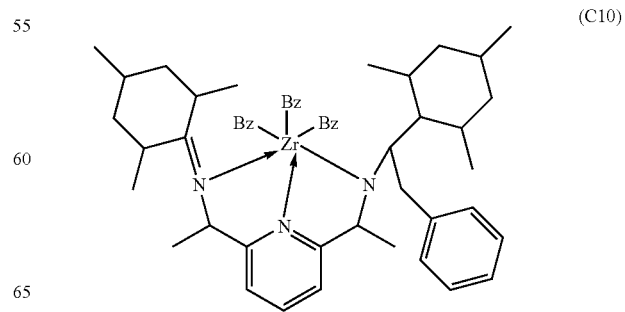

-continued

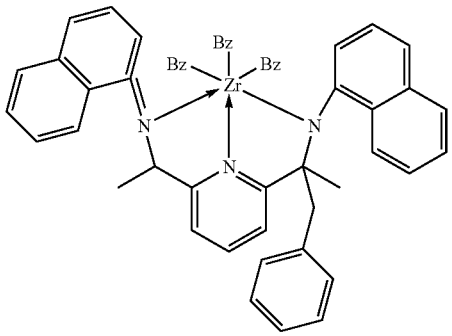

(C11)

As indicated by the above structural formulas, catalysts C9, C10 and C11 are characterized by tridentate ligand structures containing one fixed imino group and one imino group that has free rotational characteristics. Specific synthesis procedures and NMR characteristics of the catalysts C1-C11 are set forth below.

Catalyst 1: To a stirred solution of the bis-imine L1 (101.6 mg, 230 μmol) in toluene (3 mL), was slowly added a solution of Ti(CH$_2$Ph)$_4$ (100 mg., 242 μmol) in toluene (3 mL) at −10° C. over 3 minutes. Immediately, the reaction turned to a reddish brown solution. After stirring at room temperature (20° C.) for 3 days in the absence of light, the product was obtained as a dark green solution. An aliquot of the reaction mixture was used for testing in ethylene polymerization at one-atmosphere.

Catalyst 2: In a 20 ml reaction tube that was equipped with a magnetic stirrer was added the bis-imine (0.20 g., 4.52E-4E-4 moles) and the Zr(CH$_2$Ph)$_4$ (0.10 g., 2.19E-4 moles) dissolved in 3 ml of benzene-d6. Immediately, the solution turned to a dark brown solution. The vial was capped and covered with aluminum foil and left to stir at room temperature (20° C.) overnight. $^1$H—NMR (300 MHz, benzene-d6) δ 3.56 (d, J=12.9 Hz, ABX, PhCH$_2$CH$_3$), 3.30 (d, J=12.3 Hz, ABX, PhCH$_2$CH$_3$), 2.72 (d, J=12.0 Hz, Abq, Zr(CH$_2$Ph)), 2.60 (d, J=11.1 Hz, Abq, Zr(CH$_2$Ph)).

Catalysts 3-11 were synthesized in a similar fashion as catalyst 1 unless otherwise indicated below.

Catalyst 3: $^1$H—NMR (300 MHz, benzene-d6) δ 3.44 (d, J=12.9 Hz, ABX, PhCH$_2$CH$_3$), 3.02 (d, J=12.6 Hz, ABX, PhCH$_2$CH$_3$), 2.85 (d, J=13.2 Hz ABq Zr(CH$_2$Ph)), 2.60 (d, J=13.5 Hz, ABq Zr(CH$_2$Ph)).

Catalyst 4: $^1$H—NMR (300 MHz, benzene-d6) δ 4.12 (d, J=12.9 Hz, ABX, PhCH$_2$CH$_3$), 3.87 (d, J=13.2 Hz, ABX, PhCH$_2$CH$_3$), 3.28 (d, J=12.6 Hz, ABq Zr(CH$_2$Ph)), 3.11 (d, J=11.1 Hz, Abq, Zr(CH$_2$Ph)).

Catalyst 5: In a 20 ml vial equipped with a magnetic stirrer was added the bis-imine L4 (0.22 mg., 0.449 μmoles) and the Zr(CH$_2$Ph)$_4$ (20.5 mg., 0.449 μmoles) dissolved in 1 ml of benzene-d6. Immediately, the solution turned to a dark red/brown solution. The vial was capped and covered with aluminum foil and left to stir at room temperature (20° C.) overnight. Analysis of this complex was not performed. The catalyst structure is proposed due to the similarities of the reaction of Zr(CH$_2$Ph)$_4$ with similar bis-imines. An aliquot of the reaction mixture was used for testing in ethylene polymerization at one-atmosphere.

Catalyst 6: $^1$H—NMR (300 MHz, benzene-d6) δ 3.56 (d, J=12.6 Hz, ABX, PhCH$_2$CH$_3$), 3.36 (d, J=12.3 Hz, ABX, PhCH$_2$CH$_3$), 2.76 (d, J=11.4 Hz, Abq, Zr(CH$_2$Ph)), 2.65 (d, J=9.60 Hz, Abq, Zr(CH$_2$Ph)).

Catalyst 7: $^1$H—NMR (300 MHz, benzene-d6) δ 3.62 (d, J=12.9 Hz, ABX, PhCH$_2$CH$_3$), 3.04 (d, J=12.9 Hz, ABX, PhCH$_2$CH$_3$), 2.57 (d, J=12.0 Hz Abq, Zr(CH$_2$Ph)), 2.23 (d, J=10.8 Hz, Abq, Zr(CH$_2$Ph)).

Catalyst 8: In a 20 ml reaction tube equipped with a magnetic stirrer was added the bis-imine (40.9 mg., 87.6 μmoles) and the Zr(CH$_2$Ph)$_4$ (40.5 mg., 88.8 μmoles) dissolved in 2 ml of ml of benzene-d6. Immediately, the solution turned to a dark red/brown slurry. The vial was capped and covered with aluminum foil and left to stir at room temperature (20° C.) overnight. The product was obtained as a dark red/brown solution. Analysis of this complex was not performed. The catalyst structure is proposed due to the similarities of the reaction of Zr(CH$_2$Ph)$_4$ with bis-imine L5. An aliquot of the reaction mixture was used for testing in ethylene polymerization at one-atmosphere.

Catalyst 9: In a 20 ml vial equipped with a magnetic stirrer was added the bis-imine L6 (59 mg., 0.120 mmoles) and the Zr(CH$_2$Ph)$_4$ (53 mg., 0.116 mmoles) dissolved in 2 ml of toluene. Immediately, the solution turned to a dark brown solution. The vial was capped and covered with aluminum foil and left to stir at room temperature (20° C.) overnight. Analysis of this complex was not performed. The catalyst structure is proposed due to the similarities of the reaction of Zr(CH$_2$Ph)$_4$ with bis-imine L5. An aliquot of the reaction mixture was used for testing in ethylene polymerization at one-atmosphere.

Complex 10: In a 20 ml vial equipped with a magnetic stirrer was added the bis-imine L7 (44.5 mg., 0.104 mmoles) and the Zr(CH$_2$Ph)$_4$ (47.3 mg., 0.104 mmoles) and dissolved in 3 ml of benzene-d6. Immediately, the solution turned to a clear, green brown solution. The vial was capped and covered with aluminum foil and left to stir at room temperature (20° C.) overnight. Analysis of this complex was not performed. The catalyst structure is proposed due to the similarities of the reactions of Zr(CH$_2$Ph)$_4$ with similar bis-imines. An aliquot of the reaction mixture was used for testing in ethylene polymerization at one-atmosphere.

Complex 11: In a 20 ml vial equipped with a magnetic stirrer was added the bis-imine L8 (18.7 mg., 44.3 pmoles) and the Zr(CH$_2$Ph)$_4$ (20.2 mg., 44.3 μmoles) and dissolved in 3 ml of benzene-d6. Immediately, the solution turned to a yellow orange solution. The vial was capped and covered with aluminum foil and left to stir at room temperature (20° C.) overnight. Analysis of this complex was not performed. The catalyst structure is proposed due to the similarities of the reactions of Zr(CH$_2$Ph)$_4$ with similar bis-imines. An aliquot of the reaction mixture was used for testing in ethylene polymerization at one atmosphere.

The various catalysts identified above as C1-C11 were tested in polymerization runs carried out in stirred laboratory reactors available from Autoclave Engineers under the designation Zipperclave. Two reactors were employed and were operated under conditions identified below as condition B1 and condition B2. The catalyst components were tested by using an aliquot of the crude reaction product which was activated with methylalumoxane (MAO) and used in the polymerization of ethylene at one atmosphere in a toluene slurry. Since the new catalysts were tested without isolation and purification from the reaction mixtures, in general, only trace amounts of polymer were observed. It is expected that higher activities would be achieved after isolation and purification of the catalyst. However, the polymerization work as described below was useful in establishing relative activities of the various catalyst components.

A preliminary screening evaluation for the new catalysts was performed in the polymerization of ethylene at one atmosphere in a toluene solution at 25° C. Upon activation with MAO, each catalyst produced a clear, reddish brown solution as the active species. Table 1 summarizes the polymerization conditions and results. Most of the complexes were active in the polymerization of ethylene. Catalysts C2, C3 and C4 produced exothermic reactions during the polymerization. Catalyst C2 showed the highest activity producing a ΔT of 41° C. Catalyst C10 was tested by using MAO and MMAO-3A as activators, but in both cases the catalyst only produced trace amounts of polymer that was difficult to isolate.

activity is also observed for the co-polymerization of ethylene with 1-hexene (Entry 2, Table 2). Furthermore, decreasing the ethylene concentration (Entry 4, Table 2), did not affect the catalyst activity. The polymers obtained from the B2 homopolymerization conditions could not be tested for Mw in the GPC instrument due to the high viscosity of the solutions from the samples in trichlorobenzene. However, the polymer from the ethylene/1-hexene copolymerization (Entry 2, Table 2) showed an Mw of 1,493,330 from the GPC data. In addition, these polymers would not flow during the

TABLE 1

One-atmosphere Ethylene Polymerizations at 25° C.[a]

| Catalyst # | Catalyst (mg) | Activator | Time (min.) | Yield | Activity (gPE/gcat/h) | Mw | Mw/Mn |
|---|---|---|---|---|---|---|---|
| C1 | 5.0 | MAO | 30 | 0.265 g | 106 | | |
| C2 | 20.0 | MAO | 30 | 6.68 g | 668 | 156,000 | 31.2 |
| C3 | 190.0 | MAO | 30 | 4.90 g | 52 | 14,000 | 7.71 |
| C4 | 82.0 | MAO | 15 | 0.40 g | 19 | 89,000 | 11 |
| C6 | 10.0 | MAO | 60 | Trace | | | |
| C7 | 11.3 | MAO | 90 | 0.140 g | 8 | 832,000 | 67 |
| C8 | 8.1 | MAO | 120 | 85 mg | 5 | 838,000 | 66.9 |
| C9 | 56.0 | MAO | 120 | 0.340 g | 3 | | |
| C10 | 10.0 | MAO | 60 | Trace | | | |
| C10 | 5.0 | MMAO-3A[b] | 60 | Trace | | | |

[a]For each polymerization, 50 mL of toluene and 2.0 mL (95.2 mmol) of MAO (30 wt. % in toluene, Albemarle) were used.
[b]MMAO-3A (AKZO 7 wt. % in Heptane, contains about 30% of isobutyl groups).

In general, the catalyst activity trend under one atmosphere of ethylene was established as follows:

C2>>C1>C3>C4>C7>C8>C9>C6 and C10

All the catalysts produced PE with low molecular weights.

Ethylene polymerizations were conducted in the Zipperclave bench reactors under conditions identified as B1 and B2. For each catalyst, MAO was used as the activator with an Al/M ratio of 1,000 (M=Zr, Hf). The catalysts were tested without isolation and purification. The catalysts were first screened under B2 conditions as set forth in Table 2. For the polymerizations performed at 50° C. and without hydrogen (Entries 1,4,5, and 6 of Table 2), the activity trend is as follows:

C2>>C6>C3>C4

When a small quantity of hydrogen ($H_2/C_2$ 0.005) was added to the polymerization reaction and the temperature increased to 80° C., a catalyst activity increase was observed for catalyst C2 (Entry 3, Table 2). An increase of catalyst melt index test. None of the PE samples could provide rheological data due to the inability to form the plaques required for the test. Nevertheless, the DSC analysis did provide melting point data for the all of the samples and from the DSC data, the density and the percent crystallinity were calculated. In addition, C13-NMR analysis provided the microstructures of selected polymer samples (Entries 1,2, 3 and 6 of Table 2). From the DSC and C13-NMR data, it is proposed that the polymers obtained from the homo-polymerizations consisted of very high Mw linear high density PE. Although polymers from the homopolymerization and copolymerization showed equal calculated densities, the polymer from the copolymerization of ethylene and 1-hexene showed evidence of a copolymer product from C13-NMR and DSC analysis with the C13-NMR indicating 0.2 wt.% $C_6$. In addition, a lower melting temperature was observed from the DSC results (second melt peak 133.0° C.) when compared to the polymer obtained from the homo-polymerization of ethylene (second melt peak 139.3° C.) as indicated by Entries 1 and 2 in Table 2.

TABLE 2

Ethylene Polymerizations Under B2 Conditions[a]

| Entry # | Catalyst # | Cat mg | Ethylene wt. % | H2/C2 | 1-Hexene (wt. %) | Temp (° C.) | Yield | Activity (gPE/gcat/h) | Mw | Melt Index |
|---|---|---|---|---|---|---|---|---|---|---|
| 1 | C2 | 5 | 7 | 0 | 0 | 50 | 63 | 25,200 | | Too High for GPC |
| 2 | C2 | 5 | 8 | 0 | 2.44 | 80 | 120 | 48,000 | 1,493,330 | No flow |
| 3 | C2 | 5 | 7 | 0.005 | 0 | 80 | 161 | 64,400 | | Too High for GPC |
| 4 | C2 | 5 | 4 | 0 | 0 | 80 | 70 | 28,000 | | |
| 5 | C3 | 5 | 7 | 0 | 0 | 50 | 16 | 6,400 | | |
| 6 | C4 | 20 | 7 | 0 | 0 | 50 | 15 | 1,500 | | |
| 7 | C6 | 10 | 7 | 0 | 0 | 50 | 50 | 10,000 | | |

[a]Polymerization conditions: Polymerization diluent, isobutane; reaction time, 30 min.; Al/Zr, 1,000 (MAO 30 wt. % in toluene, Albemarle)
(b) Copolymerization with 1-hexene

TABLE 3

DSC Results from Ethylene Polymerizations Under B2 Conditions

| Entry # | Monomer | Catalyst # | Recrystallization Peak (° C.) | ☐H Recrystallization (J/g) | Second Melt Peak (° C.) | ☐H Second Melt (J/g) | Calculated Density | % Crystallinity |
|---|---|---|---|---|---|---|---|---|
| 1 | $C_2$ | C2 | 114.3 | −164.2 | 139.3 | 168.7 | 0.94 | 58.1 |
| 2 | $C_2$/1-hexene | C2 | 119.9 | −159.3 | 133.0 | 160.4 | 0.94 | 55.3 |
| 3 | $C_2$ | C2 | 113.3 | −187.7 | 138.0 | 180.6 | 0.94 | 62.2 |
| 4 | $C_2$ | C3 | 118.6 | −228.7 | 136.7 | 178.5 | 0.94 | 61.6 |
| 5 | $C_2$ | C4 | 115.9 | −154.3 | 142.7 | 134.2 | 0.93 | 46.3 |
| 6 | $C_2$ | C6 | 115.9 | −213.3 | 133.4 | 192.5 | 0.95 | 66.4 |

Because of the high activity of catalyst C2 in the polymerization of ethylene under one atmosphere and under B2 conditions, further screening of catalyst C2 was conducted under B1 conditions as set forth in Table 4. Initial observations showed that, without the use of hydrogen, the catalyst activity doubled under B2 polymerization conditions (Entry 1, Table 4) when compared to B1 (Entry 1, Table 2). However, analysis of the PE for GPC, melt flow or rheology was not possible due to the very high Mw. The polymerizations of ethylene in the presence of hydrogen (Entries 1 and 2, Table 4) show that catalyst C2 has a good hydrogen response. An increase of the $H_2/C_2$ ratio from 0.125 to 0.250 shows a decrease in Mw and an increase in the melt flow (Entries 1 and 2, Table 4). In addition, rheology data as set forth in Table 5 shows an increase of both the relaxation time and the breadth parameter with the increase of hydrogen.

TABLE 4

Homopolymerizations of Ethylene with Catalyst C2 Under B1 Conditions[a]

| Entry # | H2/C2 | Yield (g) | Activity (gPE/gcat/h) | Mn | Mw | Mz | Mw/Mz | Peak Mw | MI2 (g/10 min.) | MI5 (g/10 min.) | HLMI (g/10 min.) | SR5 |
|---|---|---|---|---|---|---|---|---|---|---|---|---|
| 1 | 0.000 | 132 | 52,800 | | | Too High for GPC | | | | | | |
| 2 | 0.125 | 95 | 38,000 | 9051 | 122059 | 1229625 | 13.5 | 51239 | 1.4 | 5.06 | 83.8 | 16.6 |
| 3 | 0.250 | 67 | 26,800 | 6429 | 57581 | 472493 | 9 | 4600 | 17.5 | 68.8 | >800 | 11.6 |

[a]Polymerization conditions: Polymerization diluent, hexane (3.5 wt. % ethylene content); reaction temperature, 80° C.; reaction time, 30 min.; Al/Zr, 1,000 (MAO 30 wt. % in toluene, Albemarle)

TABLE 5

Rheology Data for PE obtained from Catalyst C2 under B1 Conditions

| | Entry 3 | Entry 2 |
|---|---|---|
| Frequency Temperature Sweep | Yes | Yes |
| Ea (kJ/mol) | 34.29 | 29.67 |
| η (Pa · s) | 4.57E+03 | 1.88E+04 |
| Relaxation Time (sec) | 0 | 0.015 |
| Breadth Parameter | 0.154 | 0.236 |
| Temperature (° C.) | 190 | 190 |
| n parameter | 0 | 0 |

Heterogenization for catalyst C2 was achieved by using a MAO/SiO2 silica support having an average particle size of 50-130 microns. Up to 4 wt. % of the catalyst was immobilized on the support without any indication of catalyst leaching. The catalyst was tested in the homo-polymerization of ethylene under B1 and B configurations in the Zipperclave reactors. Under both B1 and B2 configurations, the supported catalyst showed an activity decrease when compared to the non-supported catalysts. Under B1 conditions, the supported catalyst showed a much higher hydrogen response (Entries 1 and 2, Table 6). In addition, the GPC data showed that the Mw of the polymers produced under B1 conditions decreased by about half for the supported catalyst. Furthermore, both the supported and non-supported catalysts could not produce GPC data because of the high Mw polymer produced under the B2 configuration (Entries 3 and 4, Table 6).

TABLE 6

Comparison of Catalyst C2 Supported vs. Non-supported in Ethylene Polymerization under B2 and B1 Conditions[1]

| Entry # | Polymerization Type | Catalyst | Cat mg | Tibal (mmol) | C2 wt. % | H2/C2 | Yield (g) | Activity (gPE/gcat/h) | Bulk Density | Mn | Mw | Mz | Mw/Mz | Peak Mw |
|---|---|---|---|---|---|---|---|---|---|---|---|---|---|---|
| 1 | B1 | Non-Supported | 5 | 0 | 3.5 | 0.25 | 67 | 26,800 | n.d. | 6,429 | 57,581 | 472,493 | 9 | 4600 |
| 2 | B1 | Supported[3] | 200 | 0.50 | 3.5 | 0.25 | 9 | 90 | n.d. | 3,356 | 25,484 | 200,191 | 7.6 | 1033 |
| 3 | B2 | Non-Supported | 5 | 0 | 7 | 0 | 63 | 25,200 | n.d. | | | Too High | | |
| 4 | B2 | Supported[3] | 100 | 0.63 | 8 | 0 | 31 | 620 | 0.28 | | | Too High | | |

[1] Polymerization conditions: Temperature, 80° C.; Time, 30 min.; Tibal (AKZO 25.2 wt. % in Heptane);
[2] Temperature, 50° C.; n.d., not determined;
[3] The catalyst support was prepared by mixing 0.50 g of MAO/SiO2 G-952 was slurried in 10 mL of toluene and then slowly added 22.36 mg (in 1.8 mL benzene-d6) of catalyst C2 at 20° C., after stirring overnight, it was filtered, washed with hexane and dried by vacuum and slurried in mineral oil.

The particle size distribution and polymer morphology for the PE obtained from the supported catalyst C2 under B2 polymerization condition were analyzed. The particle size distribution curve shows a narrow particle size distribution with a D50 of 126. In addition, a microscopy comparison of the MAO/SiO$_2$ to the polymer fluff shows that the particle fluff is obtained in a uniform manner with a replica effect of the particle shape obtained from the support.

Zirconium-based catalysts C2, C3 and C4 were tested in bulk propylene polymerization at 60° C. As in the polymerizations of ethylene, these catalysts were tested without isolation and purification from the reaction mixture. Upon activation with MAO, these catalysts were active in the polymerization of propylene. The results are summarized in Table 7 below. Initial results showed that these catalysts produced clear sticky gels (soluble in hexane). The activity trend was shown to be C3>C2>C4.

TABLE 7

| Catalyst # | Catalyst (mg) | Activator | Activator (mmole) | Temp (° C.) | Time (min.) | Yield | Activity (gPE/gcat/h) |
|---|---|---|---|---|---|---|---|
| C2 | 20 | MAO[a] | 9.5 | 60 | 60 | 4.38 gel | 219 |
| C3 | 10 | MAO | 9.5 | 60 | 30 | 1.18 gel | 236 |
| C4 | 53 | MAO | 9.5 | 60 | 60 | 0.94 gel | 17 |

[a] MAO (30 wt. % in toluene, Albemarle)

The Zr catalysts obtained from the (N,N,N) tridentate ligands with C$_2$ symmetry (catalysts C2 and C3) resulted in polypropylenes with moderate isotacticities characterized by 22.3% mmmm and 26.4% mmmm pentads, respectively. Catalyst C4 produced an amorphous polymer with low syndiotacticity characterized by 10.1% rrrr pentads. The pentad distributions observed for the polypropylenes produced with catalysts C2, C3 and C4 are set forth in the following table.

TABLE 8

| Pentad | Catalyst C2 | Catalyst C3 | Catalyst C4 |
|---|---|---|---|
| mmmm | 22.3 | 26.4 | 8.9 |
| mmmr | 14.7 | 15.7 | 7.7 |
| rmmr | 3.9 | 3.4 | 4.4 |
| mmrr | 17.4 | 16.7 | 9.4 |
| xmrx | 13.8 | 11.9 | 21.9 |
| mrmr | 5.5 | 4.6 | 11.9 |
| rrrr | 5.8 | 4.8 | 10.1 |
| rrrm | 7.6 | 7.1 | 15.7 |
| mrrm | 9 | 9.4 | 9.9 |

TABLE 8-continued

| Pentad | Catalyst C2 | Catalyst C3 | Catalyst C4 |
|---|---|---|---|
| % meso | 59.2 | 62.2 | 42.7 |
| % racemic | 40.8 | 37.8 | 57.3 |

Having described specific embodiments of the present invention, it will be understood that modifications thereof may be suggested to those skilled in the art, and it is intended to cover all such modifications as fall within the scope of the appended claims.

The invention claimed is:

1. A catalyst component characterized by the formula:

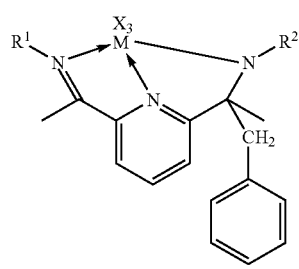

wherein $R^1$ and $R^2$ are the same or different and are each a $C_1$-$C_{20}$ alkyl group, a $C_4$-$C_{20}$ cycloalkyl group, or a substituted or unsubstituted aryl group having from 6-30 carbon atoms, M is a transition metal and X is an alkyl group, an aryl group, or a halogen.

2. The catalyst component of claim 1 characterized by the formula:

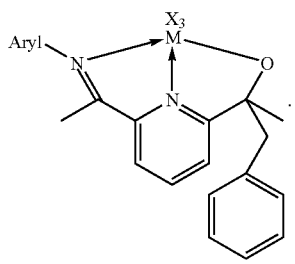

3. The catalyst component of claim 1 wherein X is a benzyl group.

4. The catalyst component of claim 3 characterized by the formula:

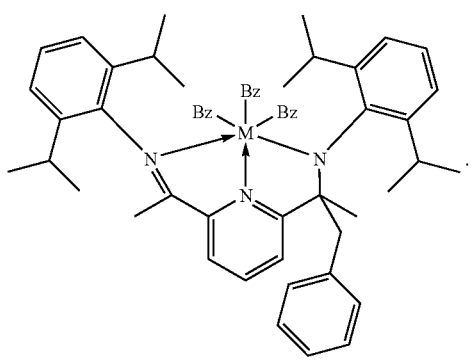

5. The catalyst component of claim 3 characterized by the formula:

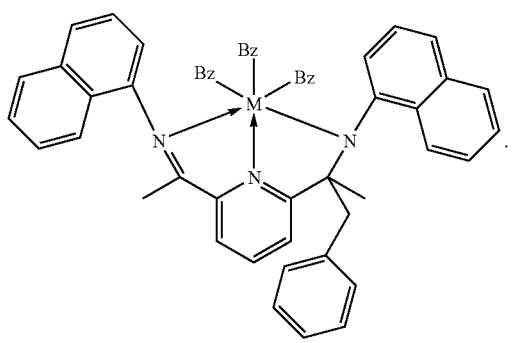

6. The catalyst component of claim 3 further characterized by the formula:

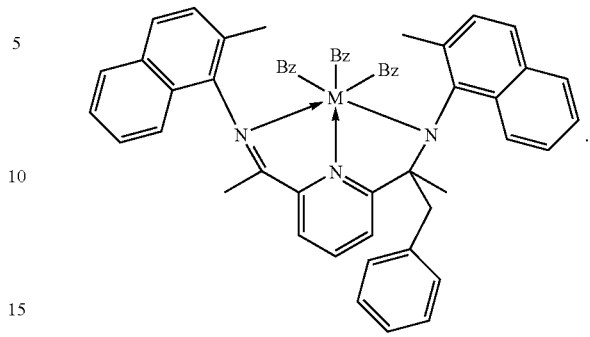

7. The catalyst component of claim 6 wherein M is zirconium.

8. The catalyst component of claim 6 wherein M is hafnium.

9. The catalyst component of claim 1 characterized by the formula:

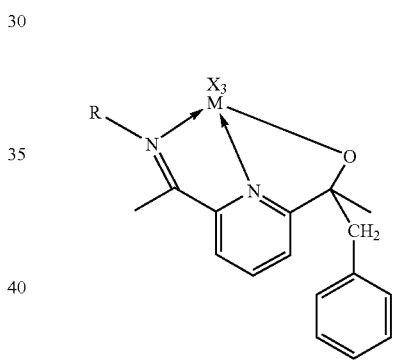

wherein R is a $C_1$-$C_{20}$ alkyl group, a $C_4$-$C_{20}$ cycloalkyl group, or a substituted or unsubstituted aryl group.

10. The catalyst component of claim 9 wherein X is a benzyl group.

11. The catalyst component of claim 1 characterized by the formula:

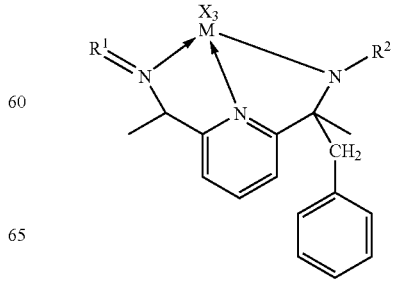

wherein $R^1$ and $R^2$ are the same or different and are each a $C_1$-$C_{20}$ alkyl group, a $C_4$-$C_{20}$ cycloalkyl group, or a substituted or unsubstituted aryl group.

12. The catalyst component of claim 11 wherein X is a benzyl group.

13. The catalyst component of claim 12 characterized by the formula:

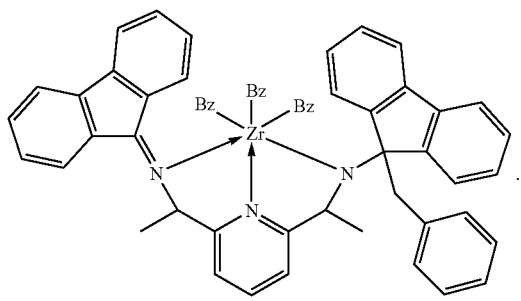

14. The catalyst component of claim 1 characterized by the formula:

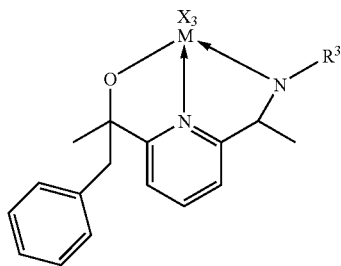

wherein $R^3$ is a substituted or unsubstituted aryl group having from 6-30 carbon atoms.

15. The catalyst component of claim 14 wherein X is a benzyl group and M is zirconium.

16. The catalyst component of claim 15 further characterized by the formula:

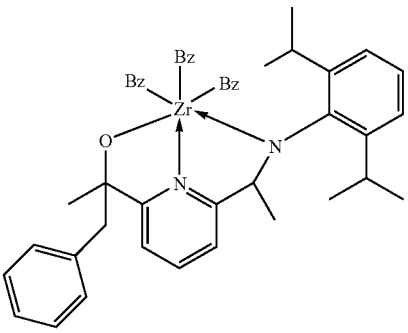

17. The catalyst component of claim 5 further characterized by the formula:

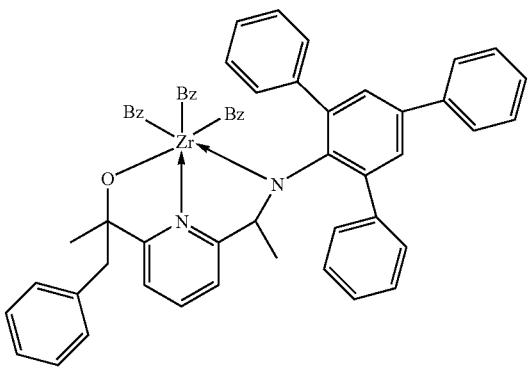

* * * * *